(12) United States Patent
Matsushita et al.

(10) Patent No.: US 6,570,015 B2
(45) Date of Patent: May 27, 2003

(54) PROCESS FOR PRODUCING 2-SUBSTITUTED THIOPYRIMIDINE-4-CARBOXYLATE

(75) Inventors: Akio Matsushita, Ube (JP); Kiyotaka Yoshii, Ube (JP); Masayoshi Oue, Ube (JP); Taku Nakamura, Ube (JP); Shuji Yamada, Ube (JP)

(73) Assignee: Ube Industries, Ltd., Ube (JP)

( * ) Notice: Subject to any disclaimer, the term of this patent is extended or adjusted under 35 U.S.C. 154(b) by 0 days.

(21) Appl. No.: 10/245,571

(22) Filed: Sep. 17, 2002

(65) Prior Publication Data

US 2003/0055252 A1 Mar. 20, 2003

(30) Foreign Application Priority Data

Sep. 19, 2001 (JP) ........................................ 2001-284635

(51) Int. Cl.[7] ............................................. C07D 239/38
(52) U.S. Cl. ...................................................... 544/318
(58) Field of Search ......................................... 544/318

Primary Examiner—John M. Ford
(74) Attorney, Agent, or Firm—Frishauf, Holtz, Goodman & Chick, P.C.

(57) ABSTRACT

There is disclosed a process for producing a 2-substituted thiopyrimidine-4-carboxylate represented by the formula (3):

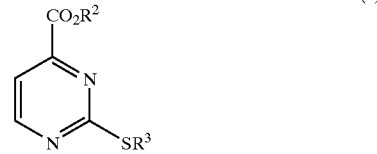

(3)

wherein $R^2$ represents a substituted or unsubstituted hydrocarbon group and $R^3$ represents a hydrocarbon group, which comprises reacting an α-keto ester compound represented by the formula (1):

$$R^1OCH=CHCOCO_2R^2 \quad (1)$$

wherein $R^1$ represents a substituted or unsubstituted hydrocarbon group, and R has the same meaning as defined above, with an isothiourea compound represented by the formula (2):

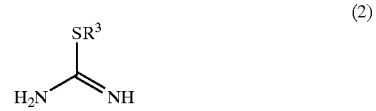

(2)

wherein $R^3$ has the same meaning as defined above.

20 Claims, No Drawings

PROCESS FOR PRODUCING 2-SUBSTITUTED THIOPYRIMIDINE-4-CARBOXYLATE

BACKGROUND OF THE INVENTION

1. Field of the Invention

The present invention relates to a process for producing a 2-substituted thiopyrimidine-4-carboxylate which is useful as a synthetic starting materials for medicine, agricultural chemicals, etc.

2. Prior Art

As a process for producing 2-substituted thiopyrimidine-4-carboxylate (carboxylic acid ester), there has been disclosed a method in which methyl isothiourea is reacted with a sodium salt of diethyl oxalacetate to prepare 6-hydroxy-2-methylthiopyrimidine-4-carboxylic acid, then, methanol is reacted therewith under acidic conditions to prepare methyl 6-hydroxy-2-methylthiopyrimidine-4-carboxylate, and then, phosphorus oxychloride is reacted therewith to prepare methyl 6-chloro-2-methylthiopyrimidine-4-carboxylate, and further, the resulting compound is subjected to hydrogen reduction in the presence of palladium black to synthesize methyl 2-methylthiopyrimidine-4-carboxylate (Japanese Provisional Patent Publication No. 57-112391, J. Org. Chem., vol. 26, 2755 (1961)).

Also, there has been disclosed a method of synthesizing ethyl 2-methylthiopyrimidine-4-carboxylate by preparing 4-iodo-2-methylpyrimidine by reacting hydriodic acid with 4-chloro-2-methylthiopyrimidine, and then, isopropyl magnesium chloride (Grignard reagent) is reacted to the resulting compound, and ethyl cyanoformate is reacted thereto (Tetrahedron, vol. 56, 265 (2000), ibid., vol. 45, 993 (1989)).

However, in either of the above-mentioned methods, there are problems that a number of the steps is so many and a yield of the resulting compound is low and the like.

SUMMARY OF THE INVENTION

An object of the present invention is to overcome the above-mentioned problems and to provide an industrially useful process for producing a 2-substituted thiopyrimidine-4-carboxylate by a simple and easy method with single step to produce a 2-substituted thiopyrimidine-4-carboxylate with a high yield.

The above object of the present invention can be accomplished by a process for producing a 2-substituted thiopyrimidine-4-carboxylate represented by the formula (3):

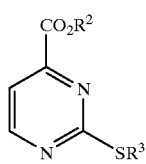

(3)

wherein $R^2$ represents a substituted or unsubstituted hydrocarbon group and $R^3$ represents a hydrocarbon group, which comprises reacting an α-keto ester compound represented by the formula (1):

$$R^1OCH=CHCOCO_2R^2 \quad (1)$$

wherein $R^1$ represents a substituted or unsubstituted hydrocarbon group, and $R^2$ has the same meaning as defined above, with an isothiourea compound represented by the formula (2):

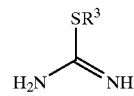

(2)

wherein $R^3$ has the same meaning as defined above.

DESCRIPTION OF THE PREFERRED EMBODIMENTS

The α-keto ester compound to be used in the reaction of the present invention is represented by the above-mentioned formula (1). In the formula (1), $R^1$ and $R^2$ each represent a substituted or unsubstituted hydrocarbon group, and for example, there may be mentioned an alkyl group preferably having 1 to 6 carbon atoms such as a methyl group, an ethyl group, a propyl group, a butyl group, etc.; an aralkyl group preferably having 7 to 12 carbon atoms such as a benzyl group, a phenethyl group, a phenylpropyl group, etc.; an aryl group preferably having 6 to 14 carbon atoms such as a phenyl group, a naphthyl group, an anthryl group, etc. Incidentally, these groups may include various kinds of isomers.

As the above-mentioned substituent, there may be mentioned, for example, an alkoxy group preferably having 1 to 6 carbon atoms such as a methoxy group, an ethoxy group, a propoxy group, a butoxy group, etc. (these groups include various kinds of isomers); a halogen atom such as a fluorine atom, a chlorine atom, a bromine atom, an iodine atom, etc. Incidentally, a number of the substituents or a position thereof is not specifically limited.

The above-mentioned α-keto ester compound can be easily synthesized by the method as disclosed in, for example, Synthesis (1988) 274, and more specifically, there may be mentioned, for example, methyl 4-methoxy-2-oxo-3-butenoate, methyl 4-ethoxy-2-oxo-3-butenoate, methyl 4-n-propoxy-2-oxo-3-butenoate, methyl 4-n-butoxy-2-oxo-3-butenoate, ethyl 4-methoxy-2-oxo-3-butenoate, ethyl 4-ethoxy-2-oxo-3-butenoate, ethyl 4-n-propoxy-2-oxo-3-butenoate, ethyl 4-n-butoxy-2-oxo-3-butenoate, n-propyl 4-methoxy-2-oxo-3-butenoate, n-propyl 4-ethoxy-2-oxo-3-butenoate, n-propyl 4-n-propoxy-2-oxo-3-butenoate, n-propyl 4-n-butoxy-2-oxo-3-butenoate, n-butyl 4-methoxy-2-oxo-3-butenoate, n-butyl 4-ethoxy-2-oxo-3-butenoate, n-butyl 4-n-propoxy-2-oxo-3-butenoate, n-butyl 4-n-butoxy-2-oxo-3-butenoate, phenyl 4-methoxy-2-oxo-3-butenoate, phenyl 4-ethoxy-2-oxo-3-butenoate, phenyl 4-n-propoxy-2-oxo-3-butenoate, phenyl 4-n-butoxy-2-oxo-3-butenoate, etc.

The isothiourea compound to be used in the reaction of the present invention is represented by the above-mentioned formula (2). In the formula (2), $R^3$ represents a hydrocarbon group, and there may be mentioned, for example, an alkyl group preferably having 1 to 6 carbon atoms such as a methyl group, an ethyl group, a propyl group, a butyl group, etc.; an aryl group preferably having 6 to 14 carbon atoms such as a phenyl group, a naphthyl group, an anthryl group, etc. Incidentally, these groups may include various kinds of isomers.

The above-mentioned isothiourea compound may specifically include, for example, an alkyl isothiourea such as methyl isothiourea, ethyl isothiourea, propyl isothiourea, butyl isothiourea, etc.; an aryl isothiourea such as phenyl isothiourea, naphthyl isothiourea, anthryl isothiourea, etc., and preferably an alkyl isothiourea is used. These isothiourea compounds can be used not only as a free isothiourea compound (including a hydrate), but also as an acidic salt such as a hydrochloride, sulfate, nitrate, phosphate, etc., and an aqueous solution thereof may be also used.

An amount of the above-mentioned isothiourea compound to be used is preferably 0.1 to 20 mol, more preferably 0.3 to 10 mol, particularly preferably 0.5 to 5 mol based on 1 mol of the α-keto ester compound.

The reaction of the present invention is preferably carried out in the presence of a base. As the base to be used, there may be mentioned, for example, amines such as triethylamine, diisopropylamine, pyridine, etc.; alkali metal alkoxides such as sodium methoxide, sodium ethoxide, etc., preferably amines, more preferably triethylamine. Incidentally, these bases may be used alone or in combination of two or more.

An amount of the base to be used is preferably 0.05 to 60 mol, more preferably 0.1 to 30 mol based on 1 mol of the α-keto ester compound.

The reaction of the present invention is carried out in the presence or absence of a solvent. As the solvent to be used, it is not particularly limited so long as it does not pertain the reaction, and there may be mentioned, for example, water; alcohols such as methanol, ethanol, n-propyl alcohol, isopropyl alcohol, n-butyl alcohol, isobutyl alcohol, t-butyl alcohol, etc.; amides such as N,N-di-methylformamide, N,N-dimethylacetamide, N,N'-dimethyl-2-imidazolidone, etc.; nitriles such as acetonitrile, propionitrile, benzonitrile, etc.; carboxylic acid esters such as methyl acetate, ethyl acetate, n-propyl acetate, n-butyl acetate, methyl propionate, ethyl propionate, n-propyl propionate, n-butyl propionate, methyl butyrate, ethyl butyrate, n-propyl butyrate, n-butyl butyrate, etc., preferably amides or nitriles are used. Incidentally, these solvents may be used alone or in combination of two or more.

An amount of the solvent to be used may be optionally adjusted depending on uniformity or stirrability of the solution, and it is preferably 1 to 500 ml, more preferably 2 to 100 ml based on 1 g of the α-keto ester compound.

The reaction of the present invention is carried out, for example, by mixing the α-keto ester compound, isothiourea compound, base and solvent in an atmosphere of an inert gas, and stirring the mixture or the like. A reaction temperature at the time is preferably 0 to 200° C., more preferably 10 to 150° C. and s reaction pressure is not specifically limited. A reaction time is not specifically limited and the reaction usually completes within 50 hours.

Also, if necessary, an additive may be added to the reaction system to heighten the reactivity, and there may be used, for example, alkali halides such as lithium chloride, lithium bromide, lithium iodide, sodium bromide, sodium iodide, potassium bromide, potassium iodide, etc.; acid anhydrides such as acetic anhydride, propionic anhydride, etc., preferably alkali halides, more preferably potassium iodide is used. Incidentally, these additives may be used alone or in combination of two or more.

An amount of the additives to be used is preferably 0.01 to 5 mol, more preferably 0.05 to 1 mol based on 1 mol of the α-keto ester compound.

Incidentally, the final product, 2-substituted thiopyrimidine-4-carboxylate can be isolated and purified by a conventional method, such as recrystallization, distillation, column chromatography, etc., after completion of the reaction, neutralization, extraction, concentration, filtration, etc.

EXAMPLES

Next, the present invention will be explained by referring to Examples, but the scope of the present invention is not limited by these examples.

Reference Example 1

(Synthesis of Methyl 4-butoxy-2-oxo-3-butenoate)

In a flask having an inner volume of 100 ml and equipped with a stirring device and a thermometer, 30.05 g (0.30 mol) of n-butyl vinyl ether and 12.25 g (0.10 mol) of methyl oxalyl chloride were charged under nitrogen atmosphere and the mixture was reacted at 10 to 20° C. for 24 hours. After completion of the reaction, 55 ml of toluene and 11.14 g (0.11 mol) of triethylamine were added thereto. Then , 50 ml of water was added t o the mixture, and the organic layer was taken out and dried over anhydrous magnesium sulfate. After filtration, the organic layer was concentrated under reduced pressure, and the concentrate was distilled under reduced pressure (80 to 122° C., 530 to 670 Pa) to obtain 12.0 g of methyl 4- butoxy-2-oxo-3-butenoate as pale yellowish orange liquid (Isolation yield based on methyl oxalyl chloride: 64.4%).

Physical properties of methyl 4-butoxy-2-oxo-3-butenoate were as follows:

$^1$H-NMR(CDCl$_3$, δ (ppm)); 0.96 (3H, t), 1.3 to 1.8 (4H, m), 3.87 (3H, s), 4.02 (2H, dd), 6.19 (1H, d), 7.89 (1H, d)

Example 1

(Synthesis of Methyl 2-methylthiopyrimidine-4-carboxylate)

In a flask having an inner volume of 50 ml and equipped with a stirring device, a thermometer and a dropping funnel were charged 9.30 g (50.0 mmol) of methyl 4-butoxy-2-oxo-3-butenoate obtained by the same method as in Reference example 1, 8.36 g (30.0 mmol) of S-methylisothiourea sulfate and 125 ml of propionitrile under nitrogen atmosphere. Then, a temperature of the liquid was cooled to 10° C. and after 5.30 g (52.0 mmol) of triethylamine was gradually added dropwise to the mixture while stirring, a temperature of the resulting mixture was raised up to 96° C. and reacted for 6 hours. After completion of the reaction, the reaction mixture was cooled to room temperature, and then, insoluble materials were filtered off and the resulting filtrate was analyzed by high performance liquid chromatography (absolute calibration curve method), it could be found that 6.91 g of methyl 2-methylthiopyrimidine-4-carboxylate was formed (Reaction yield based on methyl 4-butoxy-2-oxo-3-butenoate: 75.0%).

Further, this filtrate was purified silica gel column chromatography (filler; Wako gel C-200 (available from Wako Junyaku Co.), eluent; n-hexane/ethyl acetate=4/1 (volume ratio)) to obtain 6.40 g of methyl 2-methylthiopyrimidine-4-carboxylate as colorless powder (Isolation yield based on methyl 4-butoxy-2-oxo-3-butenoate: 69.5%).

Physical properties of methyl 2-methylthiopyrimidine-4-carboxylate were as follows.

$^1$H-NMR (CDCl$_3$, δ (ppm)); 2.62 (3H, s), 4.00 (3H, s), 7.61 (1H, d, J=4.88 Hz), 8.74 (1H, d, J=4.88 Hz)

Example 2
(Synthesis of Methyl 2-methylthiopyrimidine-4-carboxylate)

In the same manner as in Example 1 except for adding 1.67 g (10.0 mmol) of potassium iodide, the reaction was carried out as in Example 1. As a result, 7.41 g of methyl 2-methylthiopyrimidine-4-carboxylate was formed (Reaction yield based on methyl 4-butoxy-2-oxo-3-butenoate: 80.5%).

Example 3
(Synthesis of Methyl 2-methylthiopyrimidine-4-carboxylate)

In the same manner as in Example 1 except for adding 1.53 g (15.0 mmol) of acetic anhydride after one hour from initiation of the reaction, the reaction was carried out as in Example 1. As a result, 7.12 g of methyl 2-methylthiopyrimidine-4-carboxylate was formed (Reaction yield based on methyl 4-butoxy-2-oxo-3-butenoate: 77.3%).

Example 4
(Synthesis of Methyl 2-methylthiopyrimidine-4-carboxylate)

In the same manner as in Example 1 except for changing the solvent to N,N-dimethylformamide and the reaction temperature to 90° C., the reaction was carried out as in Example 1. As a result, 6.88 g of methyl 2-methylthiopyrimidine-4-carboxylate was formed (Reaction yield based on methyl 4-butoxy-2-oxo-3-butenoate: 74.7%).

Example 5
(Synthesis of Methyl 2-methylthiopyrimidine-4-carboxylate)

In the same manner as in Example 1 except for changing the solvent to acetonitrile, the reaction temperature to 82° C., and the reaction time to 16 hours, the reaction was carried out as in Example 1. As a result, 6.89 g of methyl 2-methylthiopyrimidine-4-carboxylate was formed (Reaction yield based on methyl 4-butoxy-2-oxo-3-butenoate: 74.8%).

Example 6
(Synthesis of Methyl 2-methylthiopyrimidine-4-carboxylate)

In the same manner as in Example 1 except for changing the solvent to n-butyl acetate, the reaction temperature to 133°C., and the reaction time to 25 hours, the reaction was carried out as in Example 1. As a result, 6.53 g of methyl 2-methylthiopyrimidine-4-carboxylate was formed (Reaction yield based on methyl 4-butoxy-2-oxo-3-butenoate: 70.9%).

Example 7
(Synthesis of Methyl 2-methylthiopyrimidine-4-carboxylate)

In the same manner as in Example 1 except for changing the solvent to t-butyl alcohol and the reaction temperature to 960°C., the reaction was carried out as in Example 1. As a result, 6.09 g of methyl 2-methylthiopyrimidine-4-carboxylate was formed (Reaction yield based on methyl 4-butoxy-2-oxo-3-butenoate: 66.1%).

Reference Example 2
(Synthesis of Ethyl 4-butoxy-2-oxo-3-butenoate)

In a flask having an inner volume of 100 ml and equipped with a stirring device and a thermometer were charged 30.05 g (0.30 mol) of n-butyl vinyl ether and 13.65 g (0.10 mol) of ethyl oxalyl chloride under nitrogen atmosphere, and the mixture was reacted at 10 to 200C for 24 hours. After completion of the reaction, 55 ml of toluene and 11.14 g (0.11 mol) of triethylamine were added to the mixture. Then, 50 ml of water was added to the resulting mixture, and the organic layer was taken out and dried over anhydrous magnesium sulfate. After filtration, the organic layer was concentrated under reduced pressure, and the filtrate was distilled under reduced pressure (95 to 118° C., 530 to 670 Pa) to obtain 13.3 g of ethyl 4-butoxy-2-oxo-3-butenoate as pale yellowish orange liquid (Isolation yield based on ethyl oxalyl chloride: 66.2%).

Physical properties of ethyl 4-butoxy-2-oxo-3-butenoate were as follows.

$^1$H-NMR (CDCl$_3$, δ (ppm)); 1.00 (3H, t), 1.25 to 1.83 (7H, m), 4.01 (2H, t), 4.31 (2H, dd), 6.18 (1H, d), 7.89 (1H, d)

Example 9
(Synthesis of Ethyl 2-methylthiopyrimidine-4-carboxylate)

In a flask having an inner volume of 50 ml and equipped with a stirring device, a thermometer and a dropping funnel were charged 10.01 g (50.0 mmol) of ethyl 4-butoxy-2-oxo-3-butenoate obtained by the same method as in Reference example 2, 8.36 g (30.0 mmol) of S-methylisothiourea sulfate and 125 ml of propionitrile under nitrogen atmosphere. Then, a temperature of the liquid was cooled to 10° C. and after 5.30 g (52.0 mmol) of triethylamine was gradually added dropwise to the mixture while stirring, a temperature of the resulting mixture was raised up to 96° C. and reacted for 6 hours. After completion of the reaction, the reaction mixture was cooled to room temperature, and then, insoluble materials were filtered off and the resulting filtrate was analyzed by high performance liquid chromatography (absolute calibration curve method), it could be found that 7.46 g of ethyl 2-methylthiopyrimidine-4-carboxylate was formed (Reaction yield based on ethyl 4-butoxy-2-oxo-3-butenoate: 75.3%).

Further, this filtrate was purified silica gel column chromatography (filler; Wako gel C-200 (available from Wako Junyaku Co.), eluent; n-hexane/ethyl acetate=4/1 (volume ratio)) to obtain 6.90 g of ethyl 2-methylthiopyrimidine-4-carboxylate as pale yellowish powder (Isolation yield based on ethyl 4-butoxy-2-oxo-3-butenoate: 69.6%).

Physical properties of ethyl 2-methylthiopyrimidine-4-carboxylate were as follows.

$^1$H-NMR (CDCl$_3$, δ (ppm)); 1.38 (3H, t, J=6.80 Hz), 2.63 (3H, s), 4.40 (2H, q, J=6.80), 7.59 (1H, d, J=4.88 Hz), 8.72 (1H, d, J=4.88 Hz)

Reference Example 3
(Synthesis of Ethyl 4-ethoxy-2-oxo-3-butenoate)

In a flask having an inner volume of 100 ml and equipped with a stirring device and a thermometer were charged 21.63 g (0.30 mol) of ethyl vinyl ether and 13.65 g (0.10 mol) of ethyl oxalyl chloride under nitrogen atmosphere, and the mixture was reacted at 10 to 20° C. for 24 hours. After completion of the reaction, 55 ml of toluene and 11.14 g (0.11 mol) of triethylamine were added thereto. Then, 50 ml of water was added thereto, the organic layer was taken out and dried over anhydrous magnesium sulfate. After filtration, the organic layer was concentrated under reduced pressure, and the concentrate was distilled under reduced pressure (105 to 120° C., 530 to 660 Pa) to obtain 11.3 g of ethyl 4-ethoxy-2-oxo-3-butenoate as pale yellowish orange liquid (Isolation yield based on ethyl oxalyl chloride: 65.7%).

Physical properties of ethyl 4-ethoxy-2-oxo-3-butenoate were as follows.

$^1$H-NMR (CDCl$_3$, δ (ppm)); 1.25 to 1.52 (6H, m), 4.08 (2H, 30 q), 4.35 (2H, q), 6.20 (1H, d), 7.89 (1H, d)

Example 10

(Synthesis of Ethyl 2-methylthiopyrimidine-4-carboxylate)

In a flask having an inner volume of 50 ml and equipped with a stirring device, a thermometer and a dropping funnel were charged 8.61 g (50.0 mmol) of ethyl 4-ethoxy-2-oxo-3-butenoate obtained by the same method as in Reference example 2, 8.36 g (30.0 mmol) of S-methylisothiourea sulfate and 125 ml of propionitrile under nitrogen atmosphere. Then, a temperature of the liquid was cooled to 10° C. and after 5.30 g (52.0 mmol) of triethylamine was gradually added dropwise to the mixture while stirring, a temperature of the resulting mixture was raised up to 96° C. and reacted for 6 hours. After completion of the reaction, the reaction mixture was cooled to room temperature, and then, insoluble materials were filtered off and the resulting filtrate was analyzed by high performance liquid chromatography (absolute calibration curve method), it could be found that 7.56 g of ethyl 2-methylthiopyrimidine-4-carboxylate was formed (Reaction yield based on ethyl 4-ethoxy-2-oxo-3-butenoate: 76.3%).

According to the present invention, an industrially useful process for producing 2-substituted thiopyrimidine-4-carboxylate which can produce 2-substituted thiopyrimidine-4-carboxylate with a simple and easy method, one step and high yield can be provided.

What is claimed is:

1. A process for producing a 2-substituted thiopyrimidine-4-carboxylate represented by the formula (3):

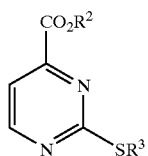

(3)

wherein R$^2$ represents a substituted or unsubstituted hydrocarbon group and R$^3$ represents a hydrocarbon group, which comprises reacting an α-keto ester compound represented by the formula (1):

$$R^1OCH=CHCOCO_2R^2 \quad (1)$$

wherein R$^1$ represents a substituted or unsubstituted hydrocarbon group, and R$^2$ has the same meaning as defined above, with an isothiourea compound represented by the formula (2):

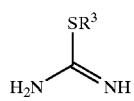

(2)

wherein R$^3$ has the same meaning as defined above.

2. The process according to claim 1, wherein the isothiourea compound is used in an amount of 0.1 to 20 mol based on 1 mol of the α-keto ester compound.

3. The process according to claim 1, wherein the isothiourea compound is used in an amount of 0.3 to 10 mol based on 1 mol of the α-keto ester compound.

4. The process according to claim 1, wherein the reaction is carried out in the presence of a base.

5. The process according to claim 4, wherein the base is used in an amount of 0.05 to 60 mol based on 1 mol of the α-keto ester compound.

6. The process according to claim 4, wherein the base is used in an amount of 0.1 to 30 mol based on 1 mol of the α-keto ester compound.

7. The process according to claim 1, wherein R$^2$ in the formula (1) is an alkyl group, an aralkyl group or an aryl group, which may be substituted by an alkoxy group or a halogen atom.

8. The process according to claim 1, wherein R$^2$ in the formula (1) is an alkyl group, an aralkyl group or an aryl group, which may be substituted by an alkoxy group or a halogen atom.

9. The process according to claim 1, wherein R$^3$ in the formula (2) is an alkyl gro up or an aryl group.

10. The process according to claim 1, wherein the α-keto ester compound is at least one selected from the group consisting of methyl 4-methoxy-2-oxo-3-butenoate, methyl 4-ethoxy-2-oxo-3-butenoate, methyl 4-n-propoxy-2-oxo-3-butenoate, methyl 4-n-butoxy-2-oxo-3-butenoate, ethyl 4-methoxy-2-oxo-3-butenoate, ethyl 4-ethoxy-2-oxo-3-butenoate, ethyl 4-n-propoxy-2-oxo-3-butenoate, ethyl 4-n-butoxy-2-oxo-3-butenoate, n-propyl 4-methoxy-2-oxo-3-butenoate, n-propyl 4-ethoxy-2-oxo-3-butenoate, n-propyl 4-n-propoxy-2-oxo-3-butenoate, n-propyl 4-n-butoxy-2-oxo-3-butenoate, n-butyl 4-methoxy-2-oxo-3-butenoate, n-butyl 4-ethoxy-2-oxo-3-butenoate, n-butyl 4-n-propoxy-2-oxo-3-butenoate, n-butyl 4-n-butoxy-2-oxo-3-butenoate, phenyl 4-methoxy-2-oxo-3-butenoate, phenyl 4-ethoxy-2-oxo-3-buten-oate, phenyl 4-n-propoxy-2-oxo-3-butenoate and phenyl 4-n-butoxy-2-oxo-3-butenoate.

11. The process according to claim 1, wherein the isothiourea compound is at least one selected from the group consisting of alkyl isothiourea and an aryl isothiourea.

12. The process according to claim 11, wherein the isothiourea compound is at least one selected from the group consisting of methyl isothiourea, ethyl isothiourea, propyl isothiourea, butyl isothiourea, phenyl isothiourea, naphthyl isothiourea and anthryl isothiourea.

13. The process according to claim 11, wherein the isothiourea compound is an acidic-salt of an isothiourea compound.

14. The process according to claim 1, wherein the reaction is carried out in the presence or absence of a solvent.

15. The process according to claim 14, wherein the solvent is at least one selected from the group consisting of water, an alcohol, an amide, a nitrile and a carboxylic acid ester.

16. The process according to claim 15, wherein the solvent is at least one selected from the group consisting of water, methanol, ethanol, n-propyl alcohol, isopropyl alcohol, n-butyl alcohol, isobutyl alcohol, t-butyl alcohol, N,N-dimethylformamide, N,N-dimethylacetamide, N,N'-dimethyl-2-imidazolidone, acetonitrile, propionitrile, benzonitrile, methyl acetate, ethyl acetate, n-propyl acetate, n-butyl acetate, methyl propionate, ethyl propionate, n-propyl propionate, n-butyl propionate, methyl butyrate, ethyl butyrate, n-propyl butyrate and n-butyl butyrate.

17. The process according to claim 14, wherein the solvent is used in an amount of 1 to 500 ml based on 1 g of the α-keto ester compound.

18. The process according to claim 14, wherein the solvent is used in an amount of 2 to 100 ml based on 1 g of the α-keto ester compound.

19. The process according to claim 1, wherein the reaction is carried out at 0 to 200° C.

20. The process according to claim 1, wherein the reaction is carried out at 10 to 150° C.

* * * * *

UNITED STATES PATENT AND TRADEMARK OFFICE
CERTIFICATE OF CORRECTION

PATENT NO. : 6,570,015 B2
DATED : May 27, 2003
INVENTOR(S) : Matsushita et al.

It is certified that error appears in the above-identified patent and that said Letters Patent is hereby corrected as shown below:

<u>Title page,</u>
Item [57], ABSTRACT,
Line 3, after formula (1), after "hydrocarbon group, and" delete "R" and insert -- $R^2$ --.

Signed and Sealed this

Thirty-first Day of May, 2005

JON W. DUDAS
*Director of the United States Patent and Trademark Office*